US010524732B2

(12) United States Patent
Kim

(10) Patent No.: US 10,524,732 B2
(45) Date of Patent: Jan. 7, 2020

(54) COMPOSITE MONITORING APPARATUS AND METHOD

(71) Applicant: UNIST (Ulsan National Institute of Science and Technology), Ulsan (KR)

(72) Inventor: Jae Joon Kim, Ulsan (KR)

(73) Assignee: UNIST (Ulsan National Institute of Science and Technology), Ulsan (KR)

( * ) Notice: Subject to any disclaimer, the term of this patent is extended or adjusted under 35 U.S.C. 154(b) by 0 days.

(21) Appl. No.: 16/074,752

(22) PCT Filed: Jan. 24, 2017

(86) PCT No.: PCT/KR2017/000829
§ 371 (c)(1),
(2) Date: Aug. 1, 2018

(87) PCT Pub. No.: WO2017/135630
PCT Pub. Date: Aug. 10, 2017

(65) Prior Publication Data
US 2019/0038230 A1    Feb. 7, 2019

(30) Foreign Application Priority Data

Feb. 5, 2016   (KR) .................. 10-2016-0015140

(51) Int. Cl.
*G08B 23/00* (2006.01)
*A61B 5/00* (2006.01)
(Continued)

(52) U.S. Cl.
CPC ............ *A61B 5/6893* (2013.01); *A61B 5/002* (2013.01); *A61B 5/02* (2013.01); *A61B 5/0205* (2013.01);
(Continued)

(58) Field of Classification Search
CPC ......... A61B 5/6893; A61B 5/002; A61B 5/02; A61B 5/0205; A61B 5/02416;
(Continued)

(56) References Cited

U.S. PATENT DOCUMENTS 6,533,184 B1 * 3/2003 Kim .................. B60H 1/00292
237/12.3 R
9,159,221 B1 * 10/2015 Stantchev .............. G08C 17/02
(Continued)

FOREIGN PATENT DOCUMENTS

KR    10-2010-0053264 A    5/2010
KR    10-2012-0084440 A    7/2012
(Continued)

OTHER PUBLICATIONS

Patent Cooperation Treaty, International Search Report and Written Opinion of the International Searching Authority, International Application No. PCT/KR2017/000829, dated Apr. 19, 2017, 12 Pages (with English Translation).

*Primary Examiner* — Zhen Y Wu
(74) *Attorney, Agent, or Firm* — Fenwick & West LLP

(57) ABSTRACT

A composite monitoring apparatus includes a biosensor configured to sense a biometric signal of a driver in a motor vehicle, an air quality sensor configured to sense an air quality inside the motor vehicle, and a control unit. The control unit determines whether data on the air quality sensed by the air quality sensor exceeds an air quality reference value when data on the biometric signal sensed by the biosensor exceeds a biometric signal reference value. Further, the control unit generates an air quality warning alarm when the data on the air quality sensed by the air quality sensor exceeds the air quality reference value.

11 Claims, 3 Drawing Sheets

(51) Int. Cl.

| | | |
|---|---|---|
| *A61B 5/02* | (2006.01) | |
| *A61B 5/145* | (2006.01) | |
| *B62D 1/04* | (2006.01) | |
| *B60K 28/02* | (2006.01) | |
| *B60K 28/06* | (2006.01) | |
| *B60Q 5/00* | (2006.01) | |
| *A61B 5/0205* | (2006.01) | |
| *A61B 5/024* | (2006.01) | |
| *A61B 5/18* | (2006.01) | |
| *B60H 1/00* | (2006.01) | |
| *B60Q 9/00* | (2006.01) | |
| *B62D 1/06* | (2006.01) | |
| *H04W 4/80* | (2018.01) | |
| *A61B 5/021* | (2006.01) | |
| *H04L 29/08* | (2006.01) | |

(52) U.S. Cl.
CPC .......... *A61B 5/02416* (2013.01); *A61B 5/145* (2013.01); *A61B 5/18* (2013.01); *A61B 5/746* (2013.01); *B60H 1/008* (2013.01); *B60K 28/02* (2013.01); *B60K 28/06* (2013.01); *B60Q 5/00* (2013.01); *B60Q 9/00* (2013.01); *B62D 1/04* (2013.01); *B62D 1/046* (2013.01); *B62D 1/06* (2013.01); *A61B 5/021* (2013.01); *A61B 5/14532* (2013.01); *A61B 5/4872* (2013.01); *A61B 2560/0242* (2013.01); *H04L 67/12* (2013.01); *H04W 4/80* (2018.02)

(58) Field of Classification Search
CPC ........... A61B 5/145; A61B 5/18; A61B 5/746; A61B 5/021; A61B 5/14532; A61B 5/4872; A61B 2560/0242; B60H 1/008; B60K 28/02; B60K 28/06; B60Q 5/00; B60Q 9/00; B62D 1/04; B62D 1/046; B62D 1/06; H04W 4/80

USPC ........................................................ 340/576
See application file for complete search history.

(56) References Cited

U.S. PATENT DOCUMENTS

| | | | |
|---|---|---|---|
| 9,183,176 | B2 | 11/2015 | Lee et al. |
| 2011/0132136 | A1* | 6/2011 | Song ................. B60R 25/04 74/552 |
| 2011/0133919 | A1* | 6/2011 | Evarts ................ B60Q 9/00 340/439 |
| 2012/0073892 | A1* | 3/2012 | Hunter ............... B60K 28/063 180/273 |
| 2013/0070043 | A1* | 3/2013 | Geva .................. B60K 28/066 348/14.02 |
| 2013/0289798 | A1* | 10/2013 | Lee .................... G06F 17/00 701/1 |
| 2013/0298716 | A1* | 11/2013 | Salvini ............... B62D 1/065 74/492 |
| 2014/0306826 | A1* | 10/2014 | Ricci .................. H04W 4/21 340/573.1 |
| 2015/0217687 | A1* | 8/2015 | Colvin, Sr. ........ B60Q 5/005 180/272 |
| 2015/0346135 | A1* | 12/2015 | Liu .................... G01N 27/403 204/407 |
| 2016/0089569 | A1* | 3/2016 | Blahnik ............. G06Q 10/0639 434/247 |
| 2016/0290979 | A1* | 10/2016 | Cogill ................ G01N 33/0004 |
| 2018/0079278 | A1* | 3/2018 | Kirpichnikov ..... B60H 1/00742 |

FOREIGN PATENT DOCUMENTS

| | | |
|---|---|---|
| KR | 10-2013/0120272 A | 11/2013 |
| KR | 10-2014/0096609 A | 8/2014 |
| KR | 10-2015-0118758 A | 10/2015 |

* cited by examiner

COMPOSITE MONITORING APPARATUS AND METHOD

RELATED APPLICATIONS

This application is a 35 U.S.C. 371 national stage filing of International Application No. PCT/KR2017/000829, filed on Jan. 24, 2017, which claims priority from Republic of Korea Patent Application No. 10-2016-0015140 filed on Feb. 5, 2016, which are hereby incorporated by reference in their entirety.

FIELD OF THE INVENTION

A composite monitoring technique in a vehicle interior environment is disclosed.

BACKGROUND OF THE INVENTION

Inside a motor vehicle, there is provided an air filter having a dust filter, an antibacterial filter and the like combined to keep indoor air comfortable. However, the air already introduced into a motor vehicle through a ventilation system or a heater is not easily discharged to the outside. The concentration of carbon dioxide inside the vehicle is higher than the concentration of carbon dioxide outside the vehicle due to the driver's breathing in a narrow indoor environment.

If a driver continuously inhales uncomfortable indoor air with a high concentration of carbon dioxide, the driver's body rhythm may be decreased, thereby causing drowsy driving.

SUMMARY OF THE INVENTION

Embodiments of the present invention provide a composite monitoring technique capable of complexly monitoring driver biometric information and air quality information.

Furthermore, embodiments of the present invention provide a composite monitoring technique capable of generating a warning alarm according to a detection data level of driver biometric information and air quality information.

In accordance with an aspect, there is provided a composite monitoring apparatus including: a biosensor configured to sense a biometric signal of a driver in a motor vehicle; an air quality sensor configured to sense an air quality inside the motor vehicle; and a control unit configured to, when data on the biometric signal sensed by the biosensor exceeds a biometric signal reference value, determine whether data on the air quality sensed by the air quality sensor exceeds an air quality reference value, and generate an air quality warning alarm when the data on the air quality sensed by the air quality sensor exceeds the air quality reference value.

The biosensor, the air quality sensor and the control unit may be mounted on a steering wheel of the motor vehicle.

Further, the biosensor, the air quality sensor and the control unit may be mounted on a steering wheel cover of the motor vehicle.

Further, the biosensor may be mounted on a portion of the steering wheel to be touched by a hand of a driver.

The biosensor may include a photoplethysmogram (PPG) sensor.

The control unit may be configured to, when the data on the biometric signal sensed by the biosensor exceeds the biometric signal reference value, determine whether the data on the air quality sensed by the air quality sensor exceeds the air quality reference value, and generate an alarm for a driver's health when the data on the air quality does not exceed the air quality reference value.

The composite monitoring apparatus may further include a communication unit configured to transmit the air quality warning alarm or the alarm for a driver's health to a user terminal device via a network.

The network may include a short-range wireless network.

The composite monitoring apparatus may be mounted on a flexible printed circuit board.

The biometric signal may include information on at least one of a heart rate, a blood pressure, a blood-sugar level and a body fat percentage of a driver.

The air quality sensor may include an air quality monitoring gas sensor.

The air quality monitoring gas sensor may include at least one of a semiconductor metal oxide sensor, an electrochemical sensor, an infrared/optical sensor and a thermopile sensor.

In accordance with another aspect, there is provided a composite monitoring method for a composite monitoring apparatus, the method including: receiving data on a biometric signal of a driver sensed by a biosensor mounted inside a motor vehicle; receiving data on an air quality sensed by an air quality sensor mounted inside the motor vehicle; determining whether the data on the air quality sensed by the air quality sensor exceeds an air quality reference value when the data on the biometric signal sensed by the biosensor exceeds a biometric signal reference value; generating an air quality warning alarm when the data on the air quality sensed by the air quality sensor exceeds the air quality reference value; and generating an alarm for a driver's health when the data on the air quality sensed by the air quality sensor does not exceed the air quality reference value.

The biosensor and the air quality sensor may be mounted on a steering wheel of the motor vehicle.

Further, the biosensor and the air quality sensor may be mounted on a steering wheel cover of the motor vehicle.

Effects of the Invention

According to an embodiment of the present invention, by monitoring the driver biometric information in combination with the air quality information and generating a warning alarm, it is possible to systematically manage the health status of a driver depending on the presence or absence of a toxic gas introduced into a motor vehicle.

Furthermore, according to an embodiment of the present invention, the sensor and the module capable of measuring the driver biometric information can be mounted inside a steering wheel of a motor vehicle, outside the steering wheel or on a steering wheel cover. Therefore, a composite monitoring environment can be easily applied to even a motor vehicle that has already been released from a factory.

DETAILED DESCRIPTION OF THE EMBODIMENTS

Advantages, features and methods for achieving them will become apparent from the embodiments, which will be described later in detail with reference to the accompanying drawings. However, the present invention is not limited to the embodiments described herein below but may be implemented in many different forms. The embodiments are provided to make complete the present invention and to completely inform the scope of the present invention to those skilled in the art to which the present invention pertains. The present invention is defined only by the claims.

In describing the embodiments of the present invention, the detailed descriptions of well-known functions or configurations will be omitted if it is determined that the detailed descriptions of well-known functions or configurations may unnecessarily make obscure the spirit of the present invention. The terms to be described later are defined in view of the functions exercised in the embodiments of the present invention and may vary depending on the intention of a user or an operator and the practice. Thus, the definition of terms shall be made based on the overall contents of the subject specification.

Hereinafter, embodiments of the present invention will be described in detail with reference to the accompanying drawings.

Figure 1:
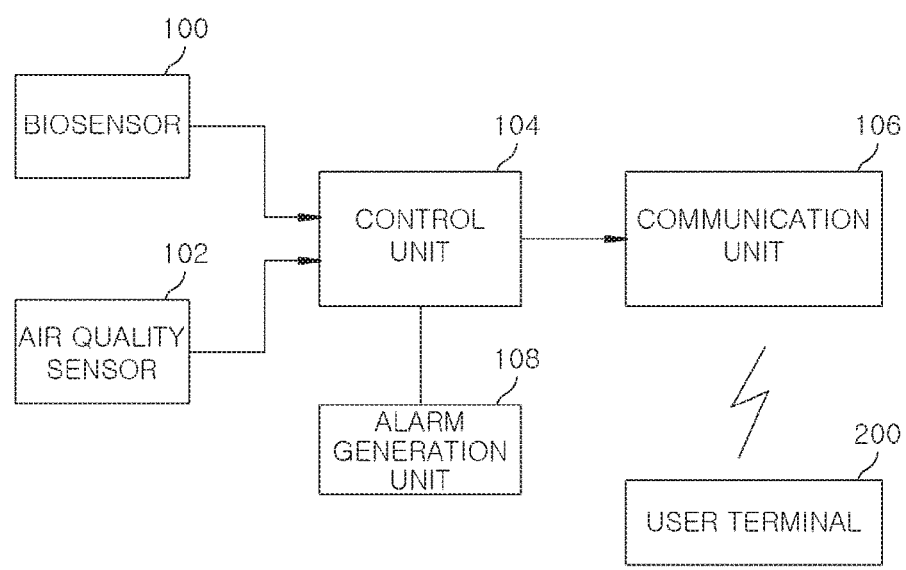
FIG. 1 is a block diagram of a composite monitoring apparatus according to an embodiment of the present invention.

FIG. 1 is a block diagram of a composite monitoring apparatus according to an embodiment of the present invention. The composite monitoring apparatus includes a biosensor 100, an air quality sensor 102, a control unit 104, a communication unit 106, an alarm generation unit 108, and the like.

As shown in FIG. 1, the biosensor 100 serves to sense a biometric signal of a driver in a motor vehicle (not shown). In this regard, the biometric signal may include at least one of the signals sensed by the biosensor 100, for example, heart rate, blood pressure, blood-sugar level and body fat percentage of a driver. The biometric signal sensed by the biosensor 100 may be transmitted to the control unit 104, which will be described later.

The air quality sensor 102 serves to sense the air quality inside a motor vehicle. The term "air quality" refers to the criterion of air cleanliness with respect to the concentration of toxic gases such as carbon monoxide (CO), hydrocarbons (HC), volatile organic compounds (VOC) and the like.

In an embodiment of the present invention, a gas sensor capable of measuring the concentration of these toxic gases, such as an air quality monitoring (AQM) gas sensor or the like, may be applied to the air quality sensor 102. The air quality information sensed by the air quality sensor 102 may be transmitted to the control unit 104 to be described later. In this case, the AQM gas sensor may include, for example, at least one of a semiconductor metal oxide sensor, an electrochemical sensor, an infrared/optical sensor and a thermopile sensor.

The control unit 104 may control the alarm generation unit 108 to generate a warning alarm according to the detection level of the biometric signal transmitted from the biosensor 100 and the air quality information received from the air quality sensor 102.

For example, the control unit 104 may determine whether the data on the air quality sensed by the air quality sensor 102 exceeds an air quality reference value when the data on the biometric signal sensed by the biosensor 100 exceeds a biometric signal reference value, and if the data on the air quality exceeds the air quality reference value, the control unit 104 may control the alarm generation unit 108 to generate an air quality warning alarm. The air quality warning alarm generated at this time may include, for example, a message that may urge a user to improve the air quality inside a motor vehicle.

In addition, the control unit 104 may determine whether the data on the air quality sensed by the air quality sensor 102 exceeds an air quality reference value when the data on the biometric signal sensed by the biosensor 100 exceeds the biometric signal reference value, and if the data on the air quality does not exceed the air quality reference value, the control unit 104 may control the alarm generation unit 108 to generate an alarm to warn the driver about the driver's health. The alarm generated at this time may include, for example, a message that may warn the driver about the driver's current healthcare status.

In the controller 104, the biometric information reference values and the air quality information reference values may be tabulated and set in advance. The control unit 104 may compare the biometric signal data and the air quality data with respective reference values to determine whether the data values exceed the respective reference values.

The communication unit 106 serves to transmit an air quality warning alarm or an alarm for a driver's health determined by the control unit 104 to a user terminal 200. The communication unit 106 may operate in a short-range wireless network environment, for example, a Bluetooth communication environment.

The alarm generation unit 108 may generate an air quality warning alarm or an alarm for a driver's health under the control of the control unit 104.

Meanwhile, the user terminal 200 may be wirelessly connected to the composite monitoring apparatus through the communication unit 106 and may transmit the air quality warning alarm or the alarm for a driver's health transmitted from the composite monitoring apparatus to the outside through a separate alarm generation means. Such a user terminal 200 may include, for example, a typical mobile device such as a smart phone, a smart pad, a tablet PC or the like, and a wearable device such as a smart watch, smart glasses, a smart ring or the like.

Figure 2:
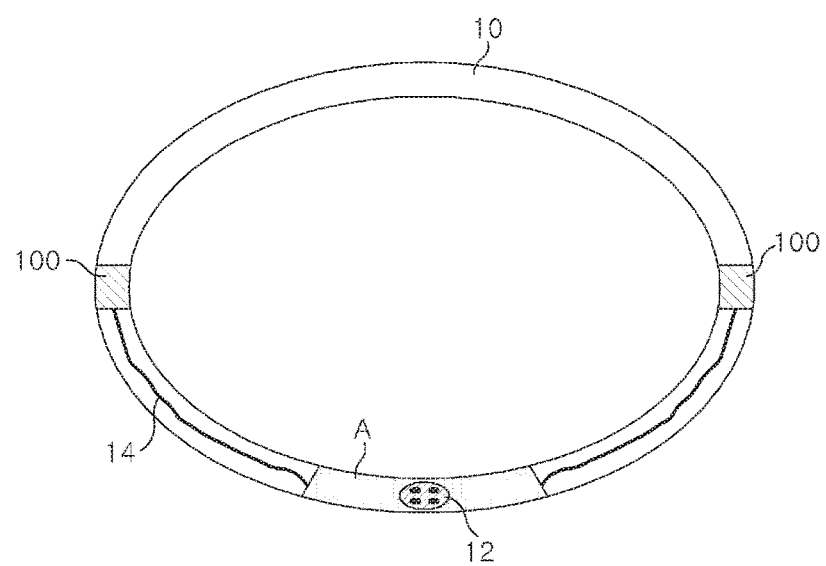
FIG. 2 is a perspective view illustrating a steering wheel of a motor vehicle or a steering wheel cover to which a composite monitoring apparatus according to the embodiment can be mounted.

FIG. 2 is a perspective view illustrating a steering wheel of a motor vehicle or a steering wheel cover on which the composite monitoring apparatus according to the embodiment of the present invention can be mounted.

The composite monitoring apparatus according to the embodiment of the present invention may be mounted in an assembly form on a steering wheel structure of a motor vehicle (inside or outside the steering wheel), or may be easily mounted on the steering wheel cover. Therefore, reference numeral 10 in FIG. 2 may denote either the steering wheel or the steering wheel cover. Hereinafter, for the sake of convenience of explanation, a case where the composite monitoring apparatus is mounted on the steering wheel will be described as an example.

As shown in FIG. 2, the biosensor 100 may be mounted at the portions of the steering wheel 10 to be touched by the driver's hands. Although two biosensors 100 are shown in FIG. 2, it is not always necessary that the two biosensor sensors 100 be touched by both hands of a driver to measure the biometric signal. For example, both hands need to be used often to measure the body fat or the like. However, the biosensor 100 may be touched by only one hand to measure the heart rate, the blood pressure, the blood-sugar level or the like.

The composite monitoring apparatus (hereinafter referred to as "composite monitoring module A") may be arranged in a module form at any arbitrary position on the steering wheel 10. The composite monitoring module A and the biosensor 100 may be electrically connected through a connecting cable 14.

An air vent 12 is formed in the composite monitoring module A and may be used to sense the air quality inside a motor vehicle.

In addition, the composite monitoring module A may be manufactured in the form of a flexible PCB (Printed Circuit Board) that can be easily mounted on the steering wheel or the steering wheel cover.

In FIG. 2, the biosensors 100 are disposed at the positions where the biosensors 100 can be touched by the driver's hands, and the composite monitoring module A is disposed at the lower end portion of the steering wheel 10. However, this is nothing more than an example and it should be noted that the composite monitoring module A may also be disposed at the position where the biosensor 100 is located. In this case, the embodiment may be implemented without using the connecting cable 14.

Figure 3:
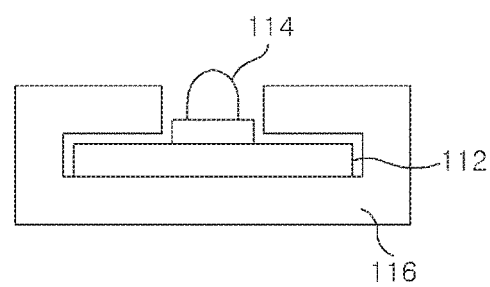
FIG. 3 is a detailed configuration diagram of a biosensor of the composite monitoring apparatus according to the embodiment.

FIG. 3 is a configuration diagram of the biosensor 100 of a composite monitoring apparatus according to the embodiment of the present invention. The biosensor 100 may include a sensor module 112, an optical element 114, a biometric signal electrode 116 and the like.

As shown in FIG. 3, the sensor module 112 may be, for example, a photoplethysmogram (PPG) sensor module.

The PPG sensor is a pulse wave measuring sensor for estimating a heart activity state by measuring the blood flow amount in a blood vessel using the optical characteristics of a living tissue. The pulse wave is a pulsating waveform that appears when blood flows out of the heart. The pulse wave can be measured based on a change in the blood flow amount due to relaxation and contraction of the heart, and a resultant change in the volume of the blood vessel. The PPG sensor uses light to observe the characteristics such as light reflectance, absorptivity, transmittance and the like of the living tissue when the volume of the blood vessel is changed. The PPG sensor may measure the pulse through the change in such characteristics.

The optical element 114 is a means for measuring the amount of light transmitted through a finger or the like of a driver or for measuring the amount of light reflected from a finger or the like. The optical element 114 may be, for example, a light emitting diode (LED), a photo transistor or a photodiode.

The biometric signal electrode 116 may be, for example, a dry-type electrode for a biometric signal and may serve to convert a bio-potential signal generated by ions in the body into an electric signal.

Therefore, the sensor module 112 may measure the PPG using the characteristic in which the current amount changes according to the amount of light irradiated to the optical element 114. The biometric signal electrode 116 may convert the PPG thus measured into an electric signal and may apply the electric signal to the control unit 104.

Figure 4:
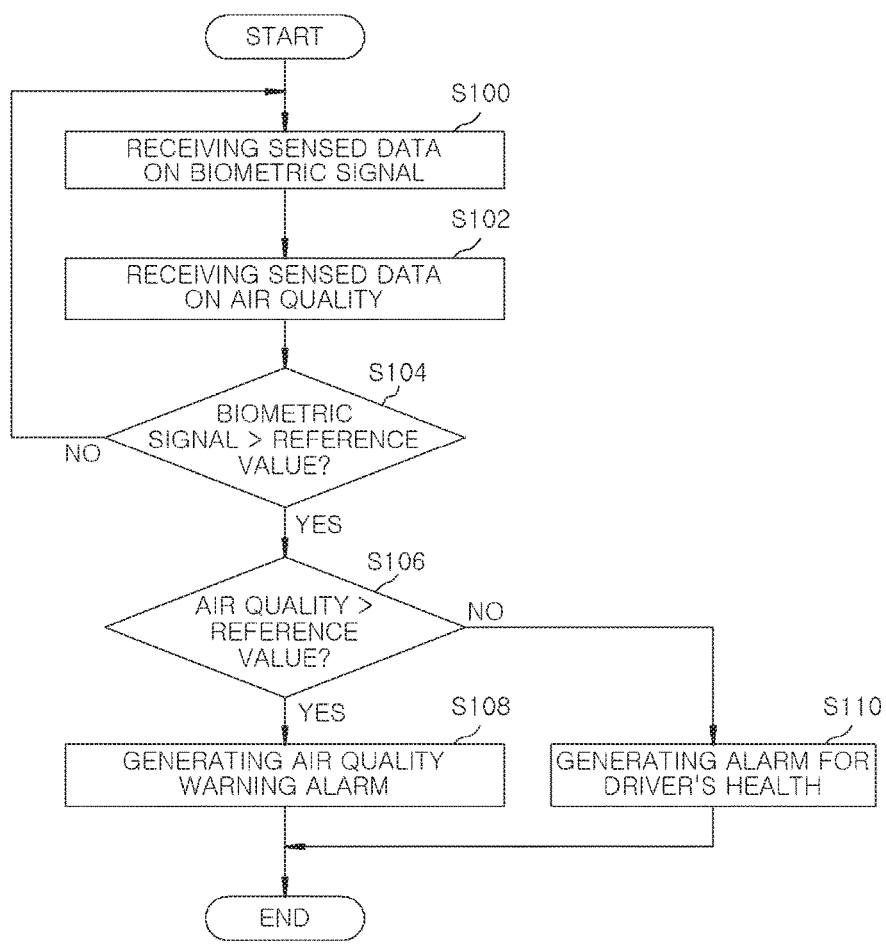
FIG. 4 is a flow chart illustrating an example of a composite monitoring process of the composite monitoring apparatus according to the embodiment.

FIG. 4 is a flowchart illustrating an example of a composite monitoring process of the composite monitoring apparatus according to the embodiment of the present invention.

As shown in FIG. 4, the control unit 104 may receive data on the driver's biometric signal sensed by the biosensor 100 mounted inside a motor vehicle, for example, on the steering wheel 10 of the motor vehicle (S100).

In addition, the control unit 104 may receive the data on the air quality sensed by the air quality sensor 102 mounted inside the motor vehicle, for example, on the steering wheel 10 of the motor vehicle (S102).

Thereafter, the control unit 104 determines whether the data on the biometric signal sensed by the biosensor 100 exceeds a biometric signal reference value (S104). When the data on the biometric signal sensed by the biosensor 100 exceeds the biometric signal reference value, the control unit 104 may determine whether the data on the air quality sensed by the air quality sensor 102 exceeds an air quality reference value (S106).

If the data on the air quality sensed by the air quality sensor 102 exceeds the air quality reference value, the control unit 104 may control the alarm generation unit 108 to generate an air quality warning alarm (S108). In this regard, the air quality warning alarm may be implemented by, for example, a guidance voice such as "activate the air conditioning system," "open the window," "set the external air inflow mode," or the like.

However, in step S106, if the data on the air quality sensed by the air quality sensor 102 does not exceed the air quality reference value, the control unit 104 may control the alarm generation unit 108 to generate an alarm for a driver's health (S110). In this regard, the alarm for a driver's health may be implemented by, for example, a guidance voice such as "the blood pressure is high," "take a break for a while," or the like.

When the air quality warning alarm or the alarm for a driver's health is transmitted to the user terminal 200 via a network, such an alarm may be implemented by outputting a guidance voice through the user terminal 200 or displaying a guidance message through a display device of the user terminal 200.

Further, in the above-described embodiment, if the data on the biometric signal sensed by the biosensor 100 exceeds the biometric signal reference value and if the data on the air quality sensed by the air quality sensor 102 exceeds the air quality reference value, the control unit 104 generates an air quality warning alarm. However, the present invention is not limited thereto. For example, if the data on the biometric signal sensed by the biosensor 100 exceeds the biometric signal reference value and if the data on the air quality sensed by the air quality sensor 102 exceeds the air quality reference value, the control unit 104 may control the alarm generation unit 108 to generate both the air quality warning alarm and the alarm for a driver's health.

According to the embodiment of the present invention as described above, the driver biometric information is monitored in combination with the air quality information to generate a warning alarm, thereby making it possible to systematically manage the health state of a driver depending on the presence or absence of a toxic gas introduced into a motor vehicle. Furthermore, the sensor and the module capable of measuring the driver biometric information can be mounted inside a steering wheel of a motor vehicle, outside the steering wheel or on a steering wheel cover.

Therefore, a composite monitoring environment can be easily applied to even a motor vehicle that has been released from a factory.

What is claimed is:

1. A composite monitoring apparatus, comprising:
   a biosensor configured to sense a biometric signal of a driver in a motor vehicle;
   an air quality sensor configured to sense an air quality inside the motor vehicle; and
   a control unit configured to, when data on the biometric signal sensed by the biosensor exceeds a biometric signal reference value, determine whether data on the air quality sensed by the air quality sensor exceeds an air quality reference value, and generate an air quality warning alarm when the data on the air quality sensed by the air quality sensor exceeds the air quality reference value,
   wherein the biosensor for sensing the biometric signal, the air quality sensor for sensing the air quality, and the control unit are mounted on a removable steering wheel cover that is mounted on a steering wheel of the motor vehicle, and
   wherein an air vent used for the air quality sensor is located at a bottom of the steering wheel.

2. The apparatus of claim 1, wherein the biosensor is mounted on a portion of the steering wheel to be touched by a hand of a driver.

3. The apparatus of claim 1, wherein the biosensor includes a photoplethysmogram (PPG) sensor.

4. The apparatus of claim 1, wherein the control unit is configured to, when the data on the biometric signal sensed by the biosensor exceeds the biometric signal reference value, determine whether the data on the air quality sensed by the air quality sensor exceeds the air quality reference value, and generate an alarm for a driver's health when the data on the air quality does not exceed the air quality reference value.

5. The apparatus of claim 4, further comprising:
   a communication unit configured to transmit the air quality warning alarm or the alarm for a driver's health to a user terminal device via a network.

6. The apparatus of claim 5, wherein the network includes a short-range wireless network.

7. The apparatus of claim 1, wherein the apparatus is mounted on a flexible printed circuit board.

8. The apparatus of claim 1, wherein the biometric signal includes information on at least one of a heart rate, a blood pressure, a blood-sugar level and a body fat percentage of a driver.

9. The apparatus of claim 1, wherein the air quality sensor includes an air quality monitoring gas sensor.

10. The apparatus of claim 9, wherein the air quality monitoring gas sensor includes at least one of a semiconductor metal oxide sensor, an electrochemical sensor, an infrared/optical sensor and a thermopile sensor.

11. A composite monitoring method for a composite monitoring apparatus, the method comprising:
    receiving data on a biometric signal of a driver sensed by a biosensor mounted inside a motor vehicle;
    receiving data on an air quality sensed by an air quality sensor mounted inside the motor vehicle;
    determining, by a control unit, whether the data on the air quality sensed by the air quality sensor exceeds an air quality reference value when the data on the biometric signal sensed by the biosensor exceeds a biometric signal reference value;
    generating an air quality warning alarm when the data on the air quality sensed by the air quality sensor exceeds the air quality reference value; and
    generating an alarm for a driver's health when the data on the air quality sensed by the air quality sensor does not exceed the air quality reference value,
    wherein the biosensor for sensing the biometric signal, the air quality sensor for sensing the air quality, and the control unit are mounted on a removable steering wheel cover that is mounted on a steering wheel of the motor vehicle, and
    wherein an air vent used for the air quality sensor is located at a bottom of the steering wheel.

\* \* \* \* \*